United States Patent
Jeannin

(10) Patent No.: US 10,537,705 B2
(45) Date of Patent: Jan. 21, 2020

(54) SYSTEM AND METHOD FOR INHIBITING MOTION SICKNESS

(71) Applicant: BOARDING RING, Ollioules (FR)

(72) Inventor: Hubert Jeannin, Ollioules (FR)

(73) Assignee: BOARDING RING, Ollioules (FR)

( * ) Notice: Subject to any disclaimer, the term of this patent is extended or adjusted under 35 U.S.C. 154(b) by 219 days.

(21) Appl. No.: 15/710,346

(22) Filed: Sep. 20, 2017

(65) Prior Publication Data
US 2019/0083739 A1    Mar. 21, 2019

(51) Int. Cl.
*A61M 21/02* (2006.01)
*F21V 23/04* (2006.01)
*A61M 21/00* (2006.01)
*F21Y 103/10* (2016.01)

(52) U.S. Cl.
CPC ......... *A61M 21/02* (2013.01); *F21V 23/0492* (2013.01); *A61M 2021/0044* (2013.01); *F21V 23/0407* (2013.01); *F21Y 2103/10* (2016.08)

(58) Field of Classification Search
CPC ............................... B64D 43/00; G01C 23/00
USPC ...................................................... 600/26–28
See application file for complete search history.

(56) References Cited

U.S. PATENT DOCUMENTS

| | | | | |
|---|---|---|---|---|
| 3,701,092 A | * | 10/1972 | Hasbrook | B64C 13/0423 340/964 |
| 5,966,680 A | * | 10/1999 | Butnaru | A61M 21/00 702/150 |
| 6,702,229 B2 | * | 3/2004 | Anderson | B64D 43/00 244/1 R |
| 9,542,147 B2 | * | 1/2017 | Colby | G06F 3/14 |
| 9,862,312 B2 | | 1/2018 | Sivak | |
| 2006/0080004 A1 | * | 4/2006 | Cheok | G01C 15/14 701/1 |
| 2016/0167672 A1 | * | 6/2016 | Krueger | H04N 13/366 340/576 |

FOREIGN PATENT DOCUMENTS

| | | |
|---|---|---|
| DE | 10 2014 210 170 A1 | 12/2005 |
| WO | WO 00/51673 A1 | 9/2000 |
| WO | WO 01/22151 A1 | 3/2001 |
| WO | WO 02/056792 A2 | 7/2002 |

* cited by examiner

*Primary Examiner* — Samuel G Gilbert
(74) *Attorney, Agent, or Firm* — Buchanan Ingersoll & Rooney PC

(57) ABSTRACT

At least two vertically-oriented lighting columns are respectively arranged on opposite lateral sides of a space that is at least partially enclosed, so as to be perceptible within a viewer's peripheral vision without obstructing or otherwise interfering with the viewer's primary field of focus. The structure that encloses the space defines a horizontal reference. A sensor detects angular movement of the structure, such as roll and/or pitch, and a controller illuminates points on the first and second lighting columns to define an angle with respect to the horizontal reference, which varies inversely relative to the sensed angle of movement. A virtual horizon represented by the defined angle provides orientation for the viewer, to reduce the likelihood of motion sickness.

12 Claims, 5 Drawing Sheets

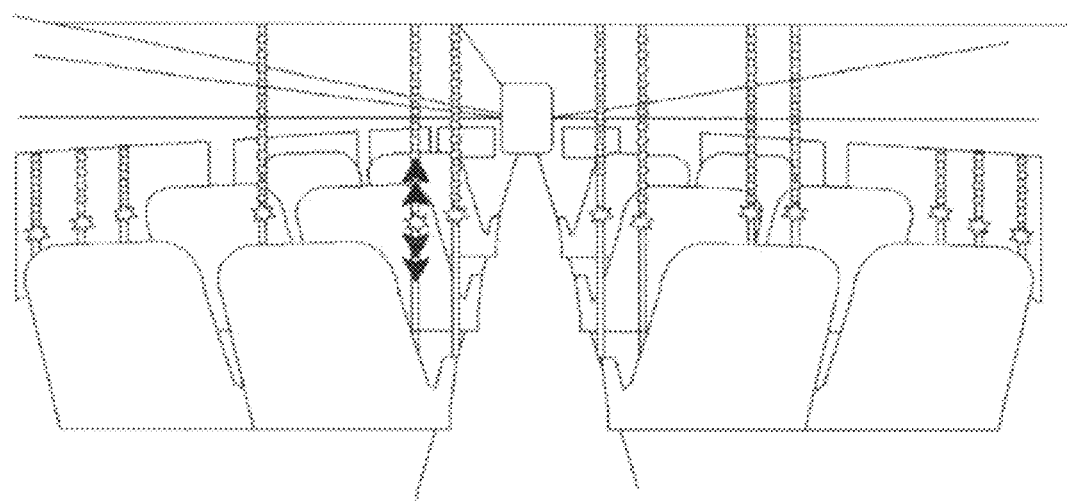
Fig. 6
Fig. 7 — 310

SYSTEM AND METHOD FOR INHIBITING MOTION SICKNESS

This disclosure involves a visual balancing system, also known as a peripheral visual identification system, that is added onto or integrated into confined, or partially-confined, mobile visual environments, such as transportation cabins (inside ships, airplanes, cars . . . ), simulators, screens or other mobile supports, to provide at least two reference points, potentially linked to gravity, essentially in the peripheral field of vision of a user, to provide visual information identical or close to common inertial perceptions (inner ear), and thus to avoid or prevent any inconvenience (such anxiety, loss of alertness, loss of attention, nausea, general motion sickness) associated with divergent perceptions of balance and sight.

The disclosure is also directed to numerous applications of the system, in particular in virtual or augmented reality, transportation, aeronautics, nautical, automobile, railway, scientific, medical, comfort, leisure, or professional fields and, military fields, but also in zoological, zootechnical or cinematographic fields.

BACKGROUND

A difference in perception between sight and balance (the inner ear) occurs when an individual is placed in a moving environment without visually perceiving this movement, and vice-versa. In such a situation, the eye perceives a stable environment inside of a moving object, for example, inside a cabin of a ship that is moving, whereas the inner ear perceives the opposite information. It feels the ship's movement. This contradiction or difference in perception is the cause of motion sickness (sea sickness, air sickness, car sickness, etc.), also called kinetosis. In essence, the information perceived by the inner ear and the information that the individual sees are in contradiction.

More particularly, an enclosure can define a reference, e.g., a two-dimensional line or a three-dimensional plane, that is normally parallel to the terrestrial horizon. Hereinafter, the reference is referred to as the enclosure's "horizontal reference." When the enclosure undergoes a rolling movement, the horizontal reference forms an angle with the terrestrial horizon, and this angle corresponds to the roll angle of the enclosure. A viewer who moves with the enclosure would then expect, based on movement of fluid in the inner ear, the horizon's angle to correspondingly change. However, when the environment of the enclosure dominates the viewer's field of vision and the expected movement of the horizon is minimally or not-at-all perceived, motion sickness can occur.

Examples of anti-kinetosis devices for addressing this situation are known in the prior art. For example, U.S. Pat. No. 6,783,237 B1 proposes, in order to act against kinetosis, glasses that contain a visual balancing device that added on or integrated to any support (i.e., glasses) that must be positioned in the individual's peripheral field of vision. It is made of a tube or pipe or any other container closed on itself, impermeable, and transparent or translucent, in which at least two substances are contained which are in different states and/or masses (for example, one being in liquid form and the other in gaseous form (stained water and air)), such that the interfaces between these substances mark visible level reference points.

Preferably, the tube closed on itself assumes the general shape of a ring or of a torus inserted or integrated into a lens or a frame with or without a lens, or even affixed by gluing or clipping. At least one of the two substances that it contains is a liquid, such that it functions in a manner fundamentally comparable to that of the inner ear. Alternatively, the visual balancing device can be manifested in a virtual or luminous image of the same type, projected or integrated into a lens of glasses, obtained by means of an electronic device consisting of, for example, a sensor (gyroscope or any other source of information or sensor of the environmental or mobile position), to detect variations of the position relative to gravity. The information, possibly after handling by a computer, is then made available to the eye or eyes by an imaging or lighting system, for example, in the form of an inside or outside perimeter of a screen, or in the form of an animation in one or more screens, wall-mounted or not, or columns, or even in the form of a lighting system, for example, by light beams.

In such a device, perceptual problems could arise, for instance due to lighting level variations. Consequently, the device is less efficient depending the contrast or lighting.

DE10 2014 210170 A1 discloses a matrix-like arrangement of LED fields in the inner panel, on the rear side of the front seat and/or in the region of the floor of a motor vehicle. An artificial horizon can be generated, which can also be varied as a function of the driving situation. Certain LEDs are driven on the backs of the front seats in such a way that an artificial horizon is obtained for changes in direction of the motor vehicle. In the case of a straight-ahead drive, selected LEDs are controlled in such a way that an artificial horizon is obtained which is approximately horizontal.

The disclosed device is configured to act on the central or front visual field, while it has been shown that to reduce or prevent kinetosis, it is better to act on the peripheral visual field. The mobilization of the central or front visual field by the use of complex images or LED matrices obstructs the viewer's voluntary focus field and causes more fatigue. Moreover, such arrangement only works for people sitting in the rear seats.

US2004/217234 A1 discloses a system for presenting to aircraft passengers a series of images that simulate or represent the view external to the aircraft, in a manner that corresponds, at least in part, with the motion the passenger feels. A passenger bay includes a display having one or more portions that present to the passengers images that move in a manner that is at least partially coupled to the movement of the aircraft. The display can include a plurality of display portions, consisting of forward display portions positioned in the backs of the seats, side display portions positioned laterally adjacent the seats, and/or top display portions located above the seats. Such system shows too much visual information, with such information being poorly delivered and therefore hardly efficient.

Additional examples of devices for displaying images to simulate actual motion are found in WO 02/056792 A2 and WO 00/51673 A. All of these known devices are configured to act on the central or front visual field, whereas it is better to act on the peripheral visual field in order to reduce or prevent kinetosis. The mobilization of the central or front visual field by the use of complex images obstructs voluntary focus field and causes more fatigue.

SUMMARY

In accordance with the principles of this disclosure, use of peripheral vision is preferable because it is the frame of the vision. The information received by peripheral vision is essentially treated in the brain (midbrain), without being taken into consideration by the viewer. The information, e.g., a point of reference, is directly and automatically given to the brain, while when using frontal vision, there is active reading by the eye before the processing of the information. Therefore, the peripheral information is more quickly processed by the brain, as a reflex. The peripheral information is therefore taken into consideration by the brain before decoding the frontal vision image seen by the viewer.

To this end, first and second vertically-oriented lighting columns are arranged on opposite lateral sides of a space that is at least partially enclosed, so as to be perceptible within a viewer's peripheral vision without obstructing or otherwise interfering with the viewer's primary field of focus. The structure that encloses the space defines a horizontal reference, e.g., a line or a plane. A sensor detects a roll angle of the structure, and a controller illuminates points on the first and second lighting columns to define an angle relative to the horizontal reference, which is the inverse of the sensed roll angle.

In a further implementation, third and fourth vertically-oriented lighting columns are respectively arranged at the sides of the space, in front of or behind the first and second vertically-oriented lighting columns. A sensor senses a pitch angle of the space, and the controller illuminates points on the first and third lighting columns, and points on the second and fourth columns, to define a second angle with respect to the horizontal reference which varies based on variations of the sensed pitch angle.

BRIEF DESCRIPTION OF DRAWING FIGURES

The scope of the present disclosure is best understood from the following detailed description of exemplary embodiments when read in conjunction with the accompanying drawings. Included in the drawings are the following figures:

FIG. 6 is a pictorial view of the implementation of the system within an airplane; and FIG. 7 is a pictorial view of the application of the system to virtual reality goggles.

Further areas of applicability of the present disclosure will become apparent from the detailed description provided hereinafter. It should be understood that the detailed description of exemplary embodiments are intended for illustration purposes only and are, therefore, not intended to limit the scope of the disclosure.

DETAILED DESCRIPTION

Figure 1:
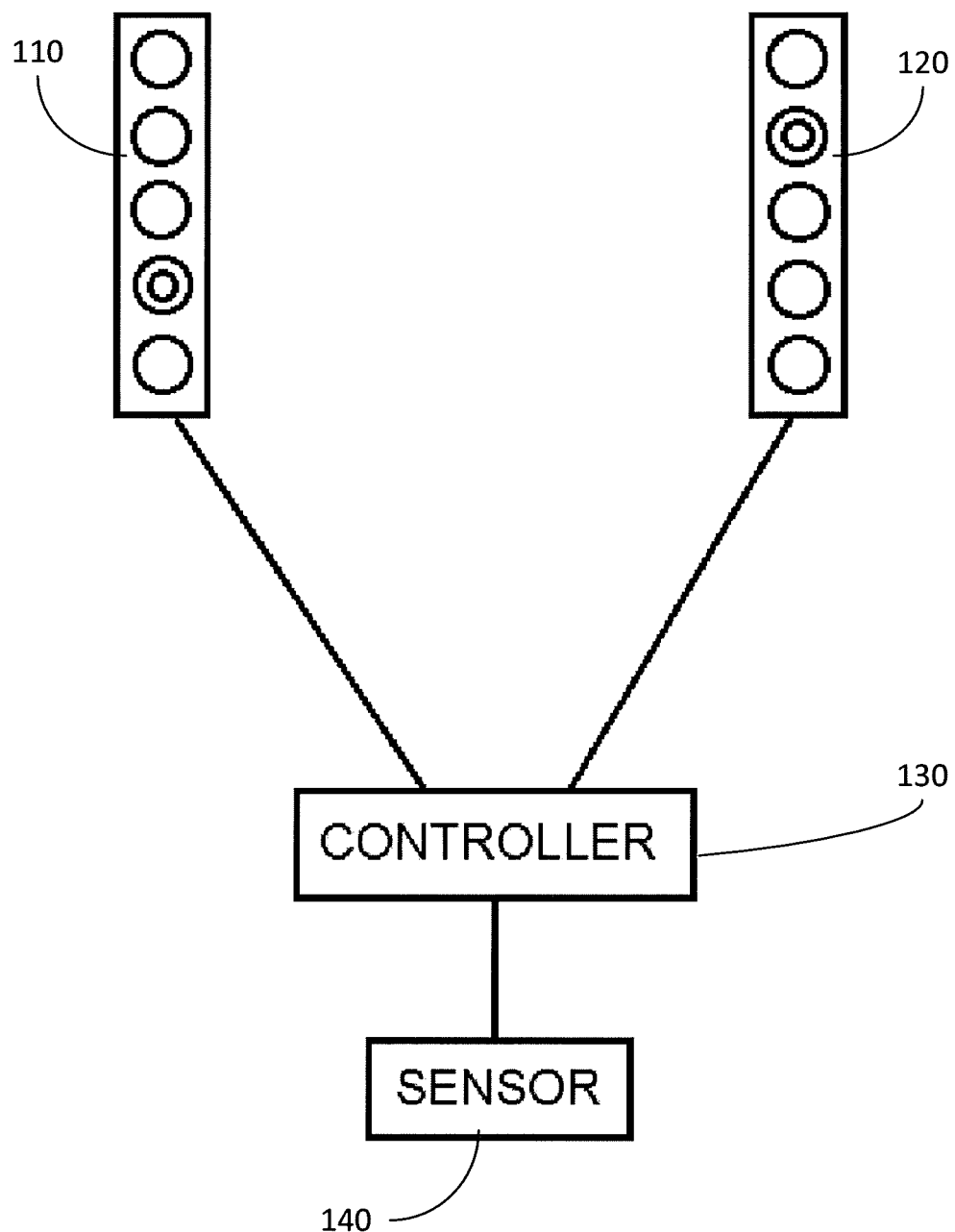
FIG. 1 is a block diagram of a first embodiment of a system in accordance with the present disclosure.

In the system and method illustrated in FIG. 1, a first vertically-oriented lighting column 110 is arranged at a left side relative to a viewer's field of vision, and a second vertically-oriented lighting column 120 is arranged at a right side relative to the viewer's field of vision. Each lighting column is configured to highlight a vertical position on the column, via illumination or brightening of one or more light elements at or near a particular vertical location. The highlighted vertical position of each location is controlled by a controller 130, based on inputs from a sensor 140, for example an inertial sensor, a gyroscope, or an accelerometer.

Each lighting column can be, for example, a linear array of Light Emitting Diodes (LEDs), but the disclosure is not limited thereto, and other types of lighting can be used. In order to highlight a particular vertical location, an LED at that location can be illuminated, with the remaining LEDs kept dark. Alternatively, the remaining LEDs can also be kept illuminated at a lower brightness. As a further option, it may be desirable to cause the LED at the point of interest to twinkle or blink to enhance the user's perception. The rod cells of the eyes are particularly sensitive to on/off information, and blinking provides a contrast in the image. As a result, the position information is more readily perceived by the blinking or twinkling.

In another implementation, all of the LEDs above, or all of the LEDs below, the highlighting LED can also be illuminated to the same brightness as the highlighting LED, with the remaining LEDs unilluminated or illuminated at a lower brightness. In this manner, a contiguous line of lights is illuminated, from one end of the column to the vertical point of interest, to increase the viewer's perception of relative vertical locations on the two sides.

When the system is incorporated, for example, into a vehicle or a pair of virtual reality goggles, the controller 130 can be embodied as a portion of the vehicle's or goggles' on-board microcomputer. Furthermore, if programmable logic is used, such logic may execute on a commercially available processing platform configured by executable software code to become a specific purpose computer or a special purpose device (e.g., programmable logic array, application-specific integrated circuit, etc.). A person having ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments. Furthermore, such a processor device may be a single processor, a plurality of processors, or combinations thereof, and may have one or more processor "cores."

The sensor 140 is a roll sensor configured to sense a roll angle of a structure at least partially enclosing a space in which the lighting columns 110 and 120 are arranged, e.g., a vehicle or a pair of virtual reality goggles. The sensor 140 can be, for example, an accelerometer or a gyroscope configured to sense the roll angle. The sensor 140 may perform other functions in the structure in which the system is incorporated.

Figure 2:
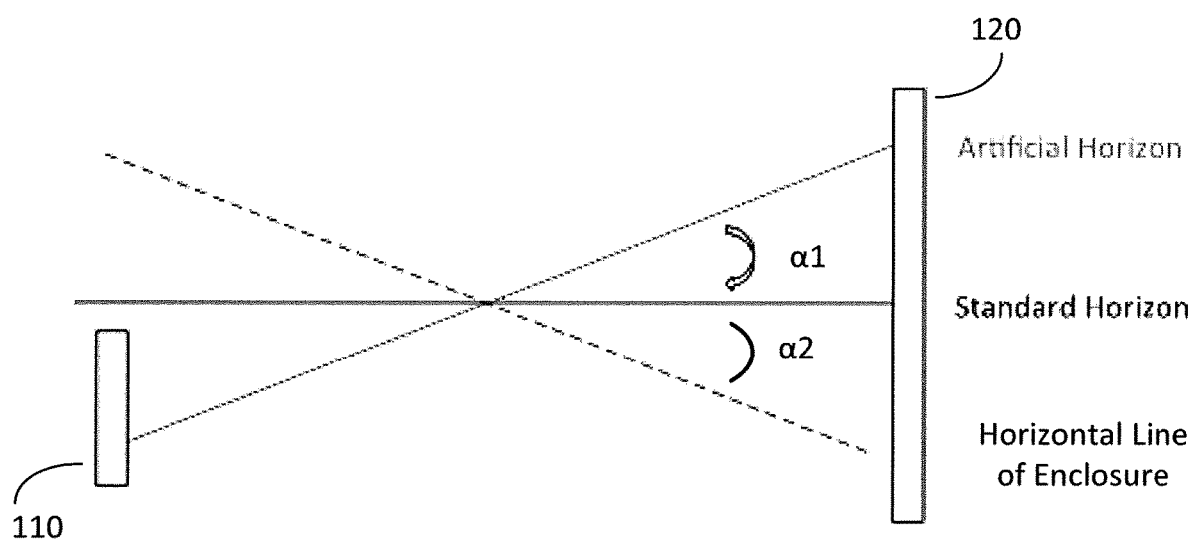
FIG. 2 is a representation of relative horizon lines illustrating the principle of operation of the disclosed system.

To inhibit motion sickness of a viewer whose field of vision is encompassed by the at least partially-enclosed space, the system functions as follows. As illustrated in FIG. 2, an enclosure defines a reference, e.g., a line of a plane, that is normally parallel to the terrestrial horizon (hereinafter its "horizontal reference"). When the enclosure undergoes a rolling movement (for example, clockwise when facing front), the horizontal reference forms an angle α1 with the horizon as viewed at the front of the enclosure, and this angle α1 corresponds to the roll angle of the enclosure. A viewer who moves with the enclosure would \ expect, based on movement of fluid in the inner ear, the horizon's angle to correspondingly change (in the example, counterclockwise when facing front). However, when the environment of the enclosure dominates the viewer's field of vision and the expected movement of the horizon is minimally or not-at-all perceived, motion sickness can occur.

To compensate for the foregoing, the system of FIG. 1 illuminates the lighting columns 110 and 120 so as to form an artificial horizon at an angle $\alpha 2$ with the horizon line, where $\alpha 2=\alpha 1$, but in the opposite direction. In some embodiments, the artificial horizon can be set at an angle that is proportional to the roll angle (e.g., $\alpha 2=0.5\alpha 1$). By providing for the artificial horizon to be defined only by lighting elements located at the lateral periphery of the viewer's field of view, motion sickness can be efficiently inhibited without interfering with the viewer's voluntary focus, or otherwise distracting the viewer. When the roll angle is zero, the lighting columns 110 and 120 will simply define a horizontal line within the enclosure (i.e., each column 110 and 120 will be illuminated at the same height).

Figure 3:
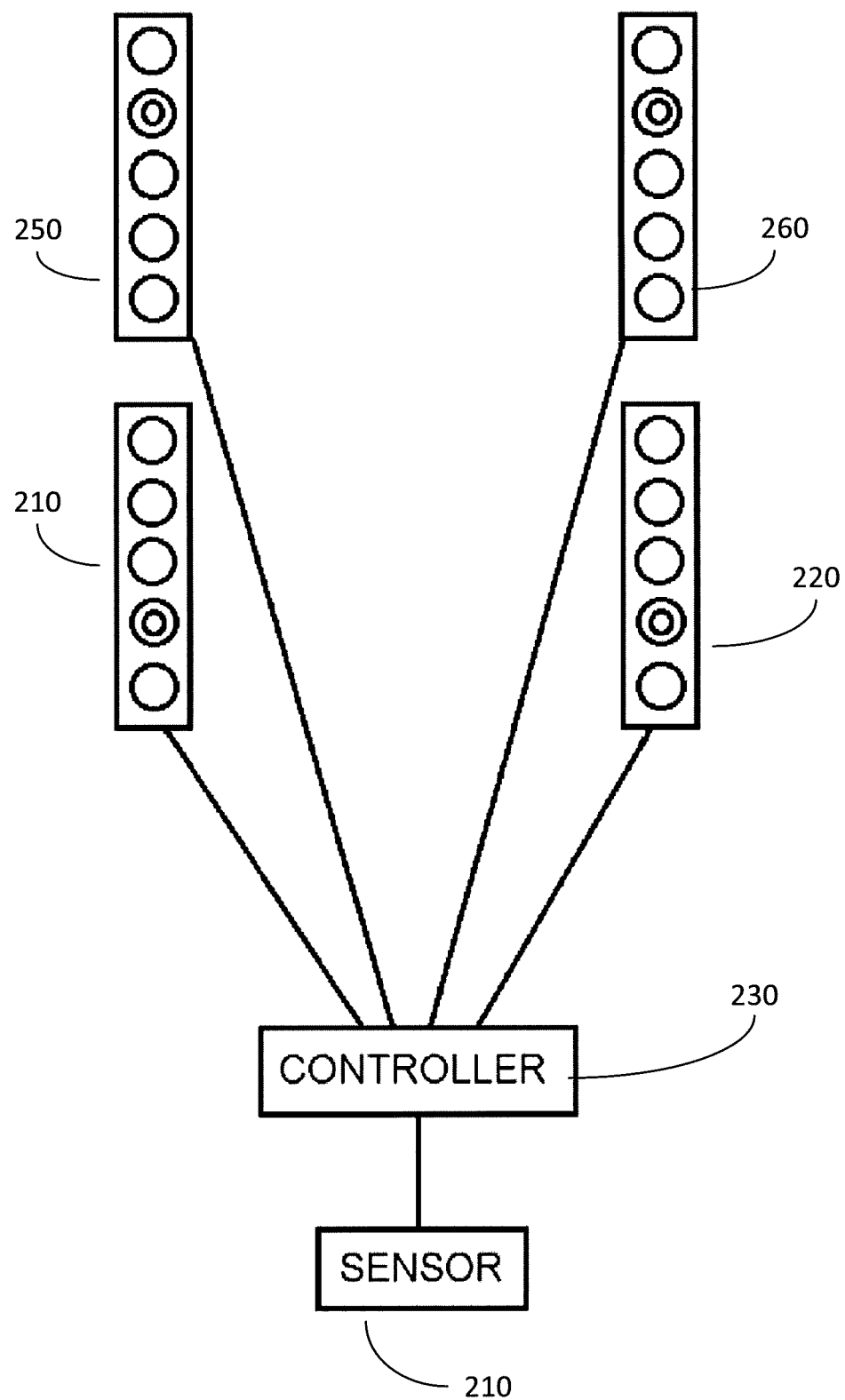
FIG. 3 is block diagram of a second embodiment of a system in accordance with the present disclosure.

From the foregoing description, it can be seen that the implementation of a system to suppress motion sickness can be effectively implemented in a simple manner, using as little as two points of light. It avoids the need to allocate large areas of the enclosure for a matrix of lights, or to display images. Moreover, efficiency and user comfort are increased by placing the light structures on the periphery of the user's field of view, and thus out main area of user focus. FIG. 3 illustrates an embodiment which can also account for pitch movement of the enclosed space, i.e., rotation about a lateral axis. The system includes a first vertically-oriented lighting column 210, a second vertically-oriented lighting column 220, a controller 230, and a sensor 240, which are arranged in the same manner and perform the same functions as the first vertically-oriented lighting column 110, the second vertically-oriented lighting column 120, the controller 130, and the sensor 140 of the FIG. 1 embodiment.

The FIG. 3 embodiment further includes a third vertically-oriented lighting column 250 and a fourth vertically-oriented lighting column 260, to provide four points of light that define a plane. The sensor 240 is configured to additionally sense the pitch angle of the enclosed space. The sensor 240 can be, for example, a two-axis sensor which can sense both roll angle and pitch angle, or can be formed from plural sensor elements, one of which senses roll angle and the other of which senses pitch angle. The sensor elements can be adjacent or can be disposed in different areas of the enclosure.

The third and fourth lighting columns 250 and 260 can have the same structural configuration as the first and second lighting columns 210 and 220, and can be mounted either in front of or behind the respective first and second lighting columns 210 and 220. When the enclosure undergoes rolling movement, the third and fourth lighting columns 250 and 260 illuminate to match the height of the other lighting column on the same respective side of the enclosure. In particular, during rolling movement, the third lighting column 250 illuminates in the same manner as the first lighting column 210 and the fourth lighting column 260 illuminates in the same manner as the second lighting column 220. Alternatively, under rolling movement, the third and fourth lighting columns 250 and 260 can remain unilluminated.

When the enclosure undergoes pitching movement, the horizontal reference forms an angle with the horizon as viewed to the side of the enclosure, and this angle corresponds to the pitch angle of the enclosed space. This can cause motion sickness for the same reasons as changes in roll angle. To compensate for this, the first and third lighting columns 210 and 250 are controlled to form an angle that inversely corresponds to that of the pitch angle. Similarly, the second and fourth lighting columns 220 and 260 are controlled to form an angle that inversely corresponds to the pitch angle. For example, if the front of the enclosure pitches downwardly, the front pair of lighting columns, e.g., 250 and 260, are controlled to indicate a vertical point that is higher than the point indicated by the rear pair of lighting columns 210 and 220, as depicted in FIG. 3. In this manner, a viewer will be able to perceive a matching artificial horizon at both peripheries based on changes in pitch angle, thereby inhibiting motion sickness based on changes in pitch angle.

In the event the enclosure in the FIG. 3 embodiment undergoes both rolling and pitching movement, the controller can either control the lighting columns 210, 220, 250, and 260 based on which angle is greater, or in a manner in which, for example, the pairs of lighting columns at the left and right peripheries form the same respective angles to accommodate for pitch, while the pairs on opposite sides are offset from each other by the appropriate angle to accommodate for roll.

Figure 4:
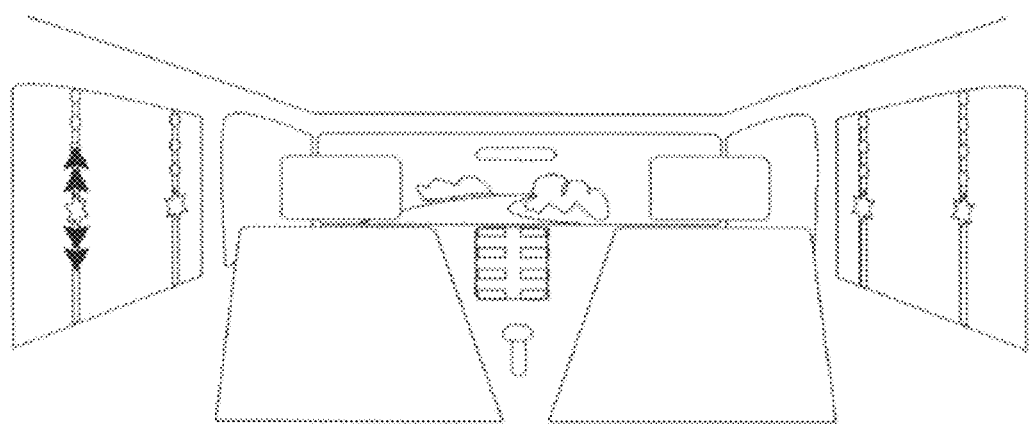
FIG. 4 is a pictorial view of the implementation of the system within an automobile.

FIG. 4 illustrates an example in which the system is adapted to an automobile. In the example, the four lighting columns of the FIG. 3 embodiment are adapted at two side windows of the automobile. Alternatively, the lighting columns might be mounted on or in the door pillars of the vehicle. In some passenger configurations, all of the passengers will be able to view the windows and the lighting columns within their peripheral vision.

Figure 5:
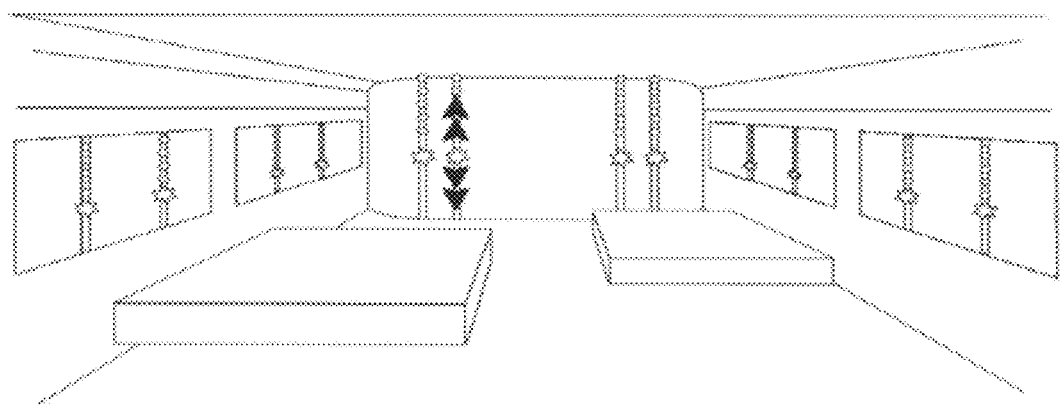
FIG. 5 is a pictorial view of the implementation of the system within a ship.

FIG. 5 illustrates an example in which the system is adapted to a ship, and FIG. 6 illustrates an example in which the system is adapted to an airplane. In these examples, there are several sets of lighting columns which can operate redundantly for passengers sitting in different areas. Furthermore, in the case of accommodating for pitch, additional lighting columns along each periphery can be controlled so that each side horizon line can be defined by several of the columns.

FIG. 7 illustrates an example in which the system is adapted to a pair of virtual reality goggles. In this example, the columns of lights 310 are located on opposite sides of the goggles, and viewable within the interior of the goggles. It has been found that, for example, when operating a drone using such goggles, the changes in the drone view, which do not match the operator's inner ear fluid, can lead to motion sickness. By providing for peripheral lighting columns using the disclosed system which define an artificial horizon line matching the operator's actual head movements, it has been found that such motion sickness can be inhibited as well.

In the case of goggles, it may be desirable to address yaw movement, i.e., rotation about a vertical axis, in addition to roll and pitch, to increase the user's comfort. For this purpose, plural columns of lights can be disposed on the side of the goggle's interior. When yaw is detected by a sensor, the columns can be illuminated in a manner that simulates movement in a direction opposite the direction of the rotation. For instance, if the user rotates his or her head in a clockwise direction, the columns can be sequentially illuminated in a counterclockwise direction.

In a preferred implementation of the principles described in this disclosure, the columns of lights are located exclusively within region of the viewers' peripheral vision, i.e., so as not to obstruct the viewers' main field of view when considering the normal situation for a particular environment. For instance, in an airplane or an automobile, the passengers face forward and therefore would be expected to look in that direction a majority of the time. Accordingly, the light columns can be mounted at appropriate locations on the side walls of the airplane cabin or automobile interior, where they can be peripherally perceived without interfering with the field of view. Similarly, in the theater of a ship, the columns of lights can be mounted on the side walls near the stage, where they can be peripherally sensed while the patrons are watching entertainment on the stage.

Techniques consistent with the present disclosure provide, among other features, systems and methods for inhibiting motion sickness. By placing the vertically-oriented columns of lights at lateral positions within the peripheral vision of a viewer, motion sickness can be tempered without adversely affecting the viewer's main field of focus. While various exemplary embodiments of the disclosed system and method have been described above, it should be understood that they have been presented for purposes of example only, not limitation.

For instance, while a linear array of LEDs has been described as one embodiment of a vertically-oriented lighting column, practical implementations of the system are not limited to such. Rather, any type of lighting structure that is capable of indicating a plurality of vertical locations, either as a single point or as a vertical column terminating at the point of interest, can be utilized. The disclosed embodiments are not exhaustive and do not limit the disclosure to the precise form disclosed. Modifications and variations are possible in light of the above teachings or may be acquired from practicing of the disclosure, without departing from the breadth or scope.

The invention claimed is:

1. A system for inhibiting motion sickness of a viewer whose field of vision is encompassed by space that is at least partially enclosed and defines a horizontal reference, said system comprising:
   a first vertically-oriented lighting column arranged in the space at a left side so as to be located within a viewer's peripheral field of vision;
   a second vertically-oriented lighting column arranged in the space at a right side so as to be located within the viewer's peripheral field of vision;
   a third vertically-oriented lighting column arranged in the space at the left side so as to be located within the viewer's peripheral field of vision and in front of or behind the first vertically-oriented lighting column;
   a fourth vertically-oriented lighting column arranged in the space at the right side so as to be located within the viewer's peripheral field of vision and in front of or behind the second vertically-oriented lighting column;
   one or more sensors configured to sense a roll angle of an enclosure for the space and a pitch angle of the enclosure for the space; and
   a controller configured to illuminate points on the first and second lighting columns to define a first angle with respect to the horizontal reference which varies inversely relative to the sensed roll angle, and to illuminate points on the first and third lighting columns, and points on the second and fourth columns, to define a second angle with respect to the horizontal reference which varies inversely relative to the sensed pitch angle.

2. The system of claim 1, wherein the space is defined by a passenger compartment of a vehicle.

3. The system of claim 1, wherein the space is defined by a pair of virtual reality goggles.

4. The system of claim 1, wherein each said lighting column comprises a linear array of lighting elements.

5. The system of claim 4, wherein the controller causes a single lighting element in each said array to be illuminated to define the first angle.

6. The system of claim 4, wherein the controller causes a contiguous plurality of lighting elements in at least one array to be illuminated, from one end of the array to the point that defines the first angle.

7. The system of claim 4, wherein the controller causes the lighting elements located at the points on the first and second lighting columns, which define the first angle, to blink or twinkle.

8. A method for inhibiting motion sickness of a viewer whose field of vision is encompassed by space that is at least partially enclosed and defines a horizontal reference, comprising:
   illuminating a first vertically-oriented lighting column at a left side of the space located within a viewer's peripheral field of vision;
   illuminating a second vertically-oriented lighting column at a right side in the space located within the viewer's peripheral field of vision;
   illuminating a third vertically-oriented lighting column at a left side of the space located within the viewer's field of vision, wherein the third vertically-oriented lighting column is spaced from the first vertically-oriented lighting column;
   illuminating a fourth vertically-oriented lighting column at a right side of the space located within the viewer's field of vision, wherein the fourth vertically-oriented lighting column is spaced from the second vertically-oriented lighting column;
   sensing a roll angle of an enclosure for the space;
   sensing a pitch angle of the enclosure for the space;
   varying the illumination of the first and second lighting columns to highlight respective points that define a first angle, relative to the horizontal reference, that is inverse to the sensed roll angle; and
   varying the illumination of the third and fourth lighting columns to highlight respective points that define a second angle, relative to the horizontal reference, that is inverse to the sensed pitch angle.

9. The method of claim 8, wherein each said lighting column comprises a linear array of lighting elements.

10. The method of claim 9, wherein the illuminating steps comprise lighting a single element in each said array to define the first angle.

11. The method of claim 9, wherein the illuminating steps comprise lighting a contiguous plurality of elements in at least one array, from one end of the array to the point that defines the first angle.

12. The method of claim 9, wherein the illuminating steps comprise causing the lighting elements located at the points on the first and second lighting columns, which define the first angle, to blink or twinkle.

* * * * *